(12) United States Patent
Lowry

(10) Patent No.: US 11,655,803 B2
(45) Date of Patent: *May 23, 2023

(54) CARBON NEGATIVE CLEAN FUEL PRODUCTION SYSTEM

(71) Applicant: Lowry Inheritors Trust, Celina, TX (US)

(72) Inventor: Scott D. Lowry, Celina, TX (US)

(73) Assignee: LOWRY INHERITORS TRUST, Sanford, NC (US)

( * ) Notice: Subject to any disclaimer, the term of this patent is extended or adjusted under 35 U.S.C. 154(b) by 76 days.

This patent is subject to a terminal disclaimer.

(21) Appl. No.: 17/308,418

(22) Filed: May 5, 2021

(65) Prior Publication Data

US 2021/0254606 A1 Aug. 19, 2021

Related U.S. Application Data

(63) Continuation-in-part of application No. 16/546,013, filed on Aug. 20, 2019, now Pat. No. 11,002,255.

(51) Int. Cl.
*F03G 7/04* (2006.01)
*C01B 13/02* (2006.01)
(Continued)

(52) U.S. Cl.
CPC ............ *F03G 7/04* (2013.01); *B01D 21/0042* (2013.01); *C01B 6/00* (2013.01); *C01B 13/0248* (2013.01);
(Continued)

(58) Field of Classification Search
CPC . F03G 7/04; F03G 7/045; F03G 7/047; F03G 7/05; Y02E 10/10; Y02E 10/30;
(Continued)

(56) References Cited

U.S. PATENT DOCUMENTS

2005/0232833 A1* 10/2005 Hardy .................... C10G 2/332
422/617
2007/0217982 A1* 9/2007 Wright .................... B01J 47/00
423/230

(Continued)

FOREIGN PATENT DOCUMENTS

WO WO-2014202855 A1 * 12/2014 ........... C25B 11/035

*Primary Examiner* — Mark A Laurenzi
*Assistant Examiner* — Xiaoting Hu
(74) *Attorney, Agent, or Firm* — Olav M. Underdal; IDP Patent Services

(57) ABSTRACT

A carbon negative clean fuel production system includes: a main platform; a heat collection device for capturing heat from a hydrothermal emissions from a hydrothermal vent on a floor of an ocean; a heat-driven electric generator; a heat distribution system including a heat absorbing material and a heat transporting pipe; anchor platforms tethered to the main platform; a mineral separator; a seawater filtration unit; a water splitting device; a sand refinery machine; a carbon removal system; and a chemical production system for producing hydrides, halides and silane. Also disclosed is a method for carbon negative clean fuel production, including: capturing heat; producing electric energy; separating minerals; filtering seawater; splitting water; refining sand; removing carbon dioxide; and producing hydrides, halides, and silane.

29 Claims, 11 Drawing Sheets

(51) Int. Cl.
*B01D 21/00* (2006.01)
*C02F 1/44* (2023.01)
*C02F 103/08* (2006.01)
*C07C 1/12* (2006.01)
*C01B 6/00* (2006.01)
*C01B 33/037* (2006.01)
*C25B 1/04* (2021.01)
*C25B 3/07* (2021.01)
*C25B 3/26* (2021.01)
*C02F 1/00* (2023.01)

(52) U.S. Cl.
CPC ............ *C01B 33/037* (2013.01); *C02F 1/441* (2013.01); *C07C 1/12* (2013.01); *C25B 1/04* (2013.01); *C25B 3/07* (2021.01); *C25B 3/26* (2021.01); *C02F 2001/007* (2013.01); *C02F 2103/08* (2013.01)

(58) Field of Classification Search
CPC ..... Y02E 60/32; Y02E 60/36; C01B 6/00–34; C01B 13/02; C01B 13/0248; C01B 33/021; C01B 33/025; C01B 33/037; C01B 33/043; C01B 3/001; C02F 1/025; C02F 1/441; C02F 1/461; C02F 1/52; C02F 2001/007; C02F 2103/08; C02F 2201/008; C02F 2303/10; C07C 1/12; C25B 1/04; C25B 3/07; C25B 3/26; C25B 15/081; Y02W 10/30; B01D 21/009; B01D 21/0042; B01D 21/01; B01D 2311/06; B01D 2311/2684; B01D 61/025; B01D 61/08; B01D 63/025; H01M 4/383; H01M 4/385
See application file for complete search history.

(56) References Cited

U.S. PATENT DOCUMENTS

| | | | |
|---|---|---|---|
| 2009/0013690 A1* | 1/2009 | Marshall | F03G 7/05 60/641.2 |
| 2009/0047072 A1* | 2/2009 | Reid | F24T 10/10 165/45 |
| 2013/0009349 A1* | 1/2013 | Chang | F27B 19/00 266/175 |
| 2016/0332167 A1* | 11/2016 | De Lange | C02F 1/482 |
| 2017/0321656 A1* | 11/2017 | Eisenberger | F03B 13/00 |

* cited by examiner

System for Carbon Negative Clean Fuel Production

Mineral Separator

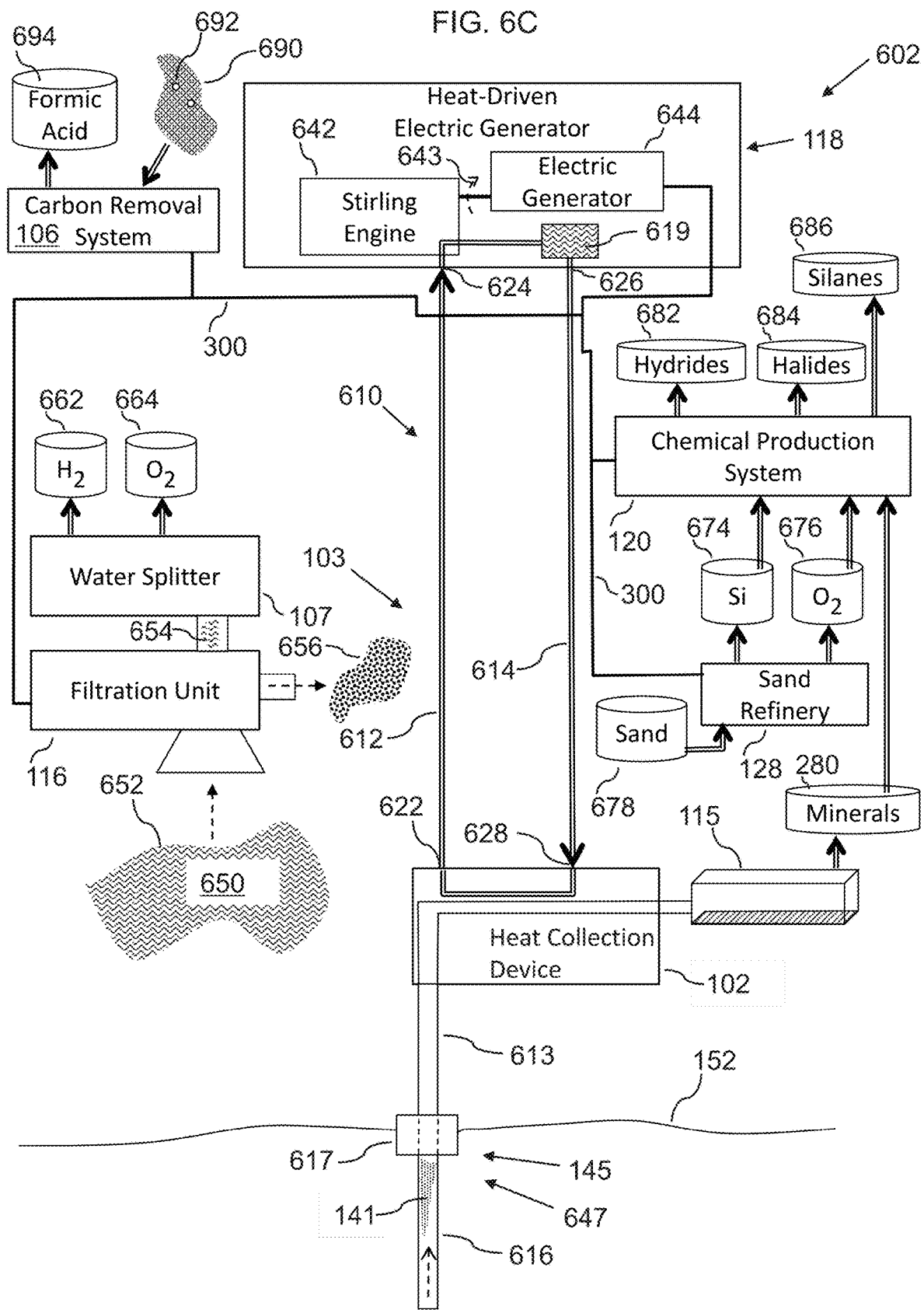

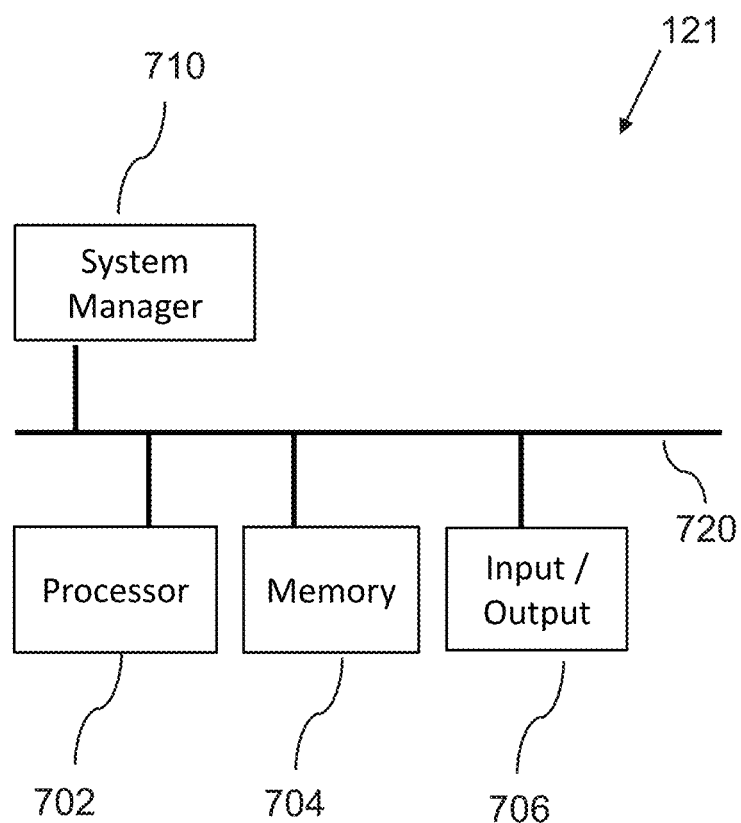

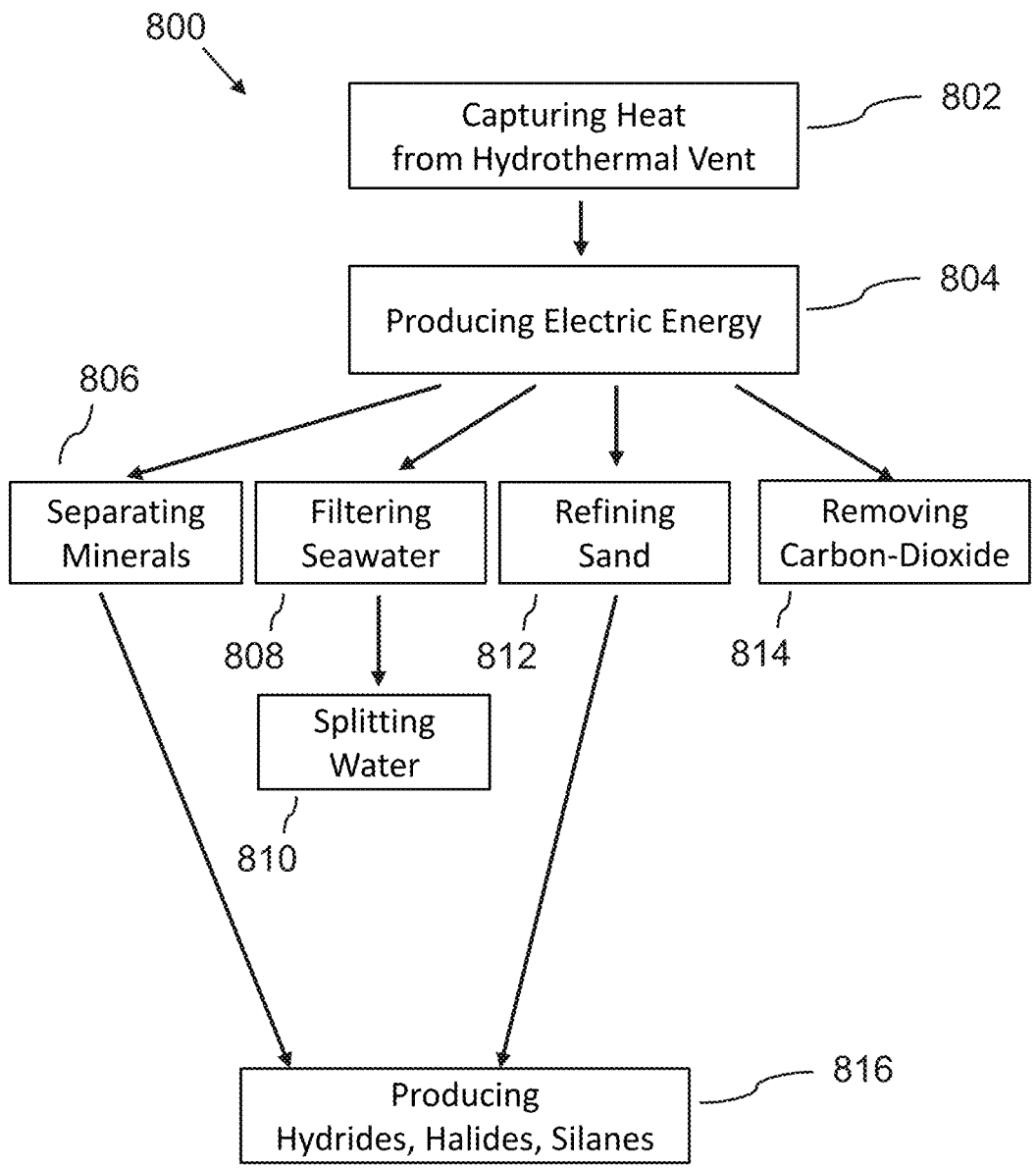

CARBON NEGATIVE CLEAN FUEL PRODUCTION SYSTEM

CROSS-REFERENCE TO RELATED APPLICATIONS

This U.S. Non-Provisional application is a Continuation-In-Part of U.S. Non-Provisional application Ser. No. 16/546,013, filed Aug. 20, 2019; which is hereby included herein by reference in its entirety.

FIELD OF THE INVENTION

The present invention relates generally to energy harvesting, and more particularly, to harvesting energy from subsea hydrothermal vents, for conversion into alternative fuel stores.

BACKGROUND OF THE INVENTION

Hydrothermal vents are fissures in the seafloor from which heated water issues. Hydrothermal vents are found in areas associated with movement of tectonic plates and ocean basin hotspots. These vents are located on the plate expansion zones known as the mid-ocean ridges and on the plate subduction zones known as the ring of fire. The number of hydrothermal vents is unknown, but experts have recently placed the number as high as 10 million.

The Woods Hole Institute keeps a database of known hydrothermal vents including their GPS position, their depth, active status and other known data. For example, the Alarcon rise vent field is listed in the database at a latitude of 23.3553 and longitude of −108.5443 in the gulf of California with a maximum known temperature of 354 degrees Celsius (669 Fahrenheit.)

Plumes emanating from hydrothermal vents are rich in minerals. The mineral content of the plumes is expected to vary greatly based on the geology of the location. Water from the ocean infiltrates the oceans floor in what is called a recharge zone. As it moves deeper and closer to the heated subsurface magma chamber, the intense heat dissolves minerals in the water in the recharge zone. As the heat builds, the water begins to rise into a common exit called the hot focused flow. The water temperature of this hot focused flow can reach 350 degrees Celsius, or nearly 700 degrees Fahrenheit, while the nearby water at the depth of many hydrothermal vents can be as cold as −2 degrees Celsius (28.4 degrees Fahrenheit).

The dissolved minerals in the superheated waters exiting the vent give the appearance of smoke. Hydrothermal vents are often classified by their smoke color as being either black smokers or white smokers. The difficulty of accessing these vents has limited studies as to their mineral contents, temperature variations, surrounding biology and other factors. The extreme temperatures and pressures surrounding many hydrothermal vents require highly specialized equipment for even simple tasks.

Global demand for energy and clean energy fuels is rising. It is becoming increasingly difficult to find new energy sources and existing sources are insufficient to meet our long-term needs creating the ever-increasing use of fossil fuels thereby threatening the very existence of life on this planet through global warming.

There has been interest in finding a new fuel to replace oil for some time. Many candidates have been proposed, from corn to solar. One of the most promising new fuels is silane, a fuel made from the silicon found in sand. Silane is a gas at room temperature. It decomposes at relatively low temperatures and pressures to liberate hydrogen and deposit high purity silicon's. Silane is flammable and pyphoric (autoigniting in air). It is also considered an excellent hydrogen carrier. Some properties of silane, disilane, and trisilane make them difficult to use as a gasoline replacement in cars, but they are suitable for highly controllable environments like electricity generating power plants, trains and ships.

As such, considering the foregoing, it may be appreciated that there continues to be a need for novel and improved devices and methods for carbon negative clean fuel production.

SUMMARY OF THE INVENTION

The foregoing needs are met, to a great extent, by the present invention, wherein in aspects of this invention, enhancements are provided to the existing models of fuel production.

In an aspect, a carbon negative clean fuel production system can include:
 a) a main platform, which can be positioned on or below the ocean surface. In some configurations the main platform may reside on land in workable proximity to the hydrothermal vent, or on a floor of the ocean;
 b) a heat collection device, which can be configured to capture heat from hydrothermal emissions from a hydrothermal vent on a floor of an ocean;
 c) a heat-driven electric generator, which is configured to receive the heat from the hydrothermal vent and produce electric energy, wherein the heat-driven electric generator is mounted on a surface of a platform; and
 d) a heat distribution system, comprising:
  a heat absorbing material and at least one heat transporting pipe, comprising:
   a heat transport segment; and
   a return flow segment;
  such that the heat absorbing material flows through the heat collection device, such that the heat absorbing material absorbs the heat from the hydrothermal emissions; and
  such that the heat absorbing material flows through the heat-driven electric generator, such that the heat-driven electric generator produces the electric energy from the heat of the heat absorbing material.

In another related embodiment, the carbon negative clean fuel production system can further include:
 a) at least one anchor platform; and
 b) at least one tether;
 wherein the anchor platform can be configured to be positioned on a floor of the ocean; and wherein a first end of the tether is connected to the platform and a second end of the tether is connected to the platform;
 such that the platform is secured in position.

In yet another related aspect, the heat-driven electric generator can be a Stirling generator, which can include:
 a) a Stirling engine, which is configured to generate mechanical energy from the heat absorbing material; and
 b) an electrical generator, which is configured to convert the mechanical energy into the electric energy.

In another related aspect, the carbon negative clean fuel production system can further include:
 a mineral separator, which is an enclosure that comprises riffles along an inner bottom of the enclosure;
 wherein an input opening of the enclosure receives the hydrothermal emissions from the hydrothermal vent, such that the hydrothermal emissions pass through the enclosure, such that solid minerals are deposited in the riffles and remaining emissions are ejected from an output opening of the enclosure.

In yet another related aspect, the carbon negative clean fuel production system can further include:

a seawater filtration unit, which is configured to filter seawater from the ocean by reverse osmosis, to produce filtered freshwater and solutes which include brine and solute minerals.

In another related aspect, the carbon negative clean fuel production system can further include:

a water splitting device, which is configured to use the electric energy generated by the heat-driven electric generator to split the filtered freshwater into hydrogen and oxygen, for example by a process of electrolysis.

In another related aspect, the carbon negative clean fuel production system can further include:

a sand refinery machine, which is configured to refine sand to produce chemical components, including silicon and oxygen.

In another related aspect, the carbon negative clean fuel production system can further include:

a carbon removal system, which is configured to use the electric energy generated by the heat-driven electric generator to pump in atmospheric air, and to produce formic acid from carbon dioxide in the atmospheric air, thereby reducing a concentration of carbon dioxide in the atmospheric air.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 6C is a schematic diagram illustrating a carbon negative clean fuel production system, according to an embodiment of the invention.

FIG. 7 is a schematic diagram illustrating a system control unit, according to an embodiment of the invention.

FIG. 8 is a flowchart illustrating steps that may be followed, in accordance with one embodiment of a method or process of carbon negative clean fuel production.

DETAILED DESCRIPTION

Figure 1:
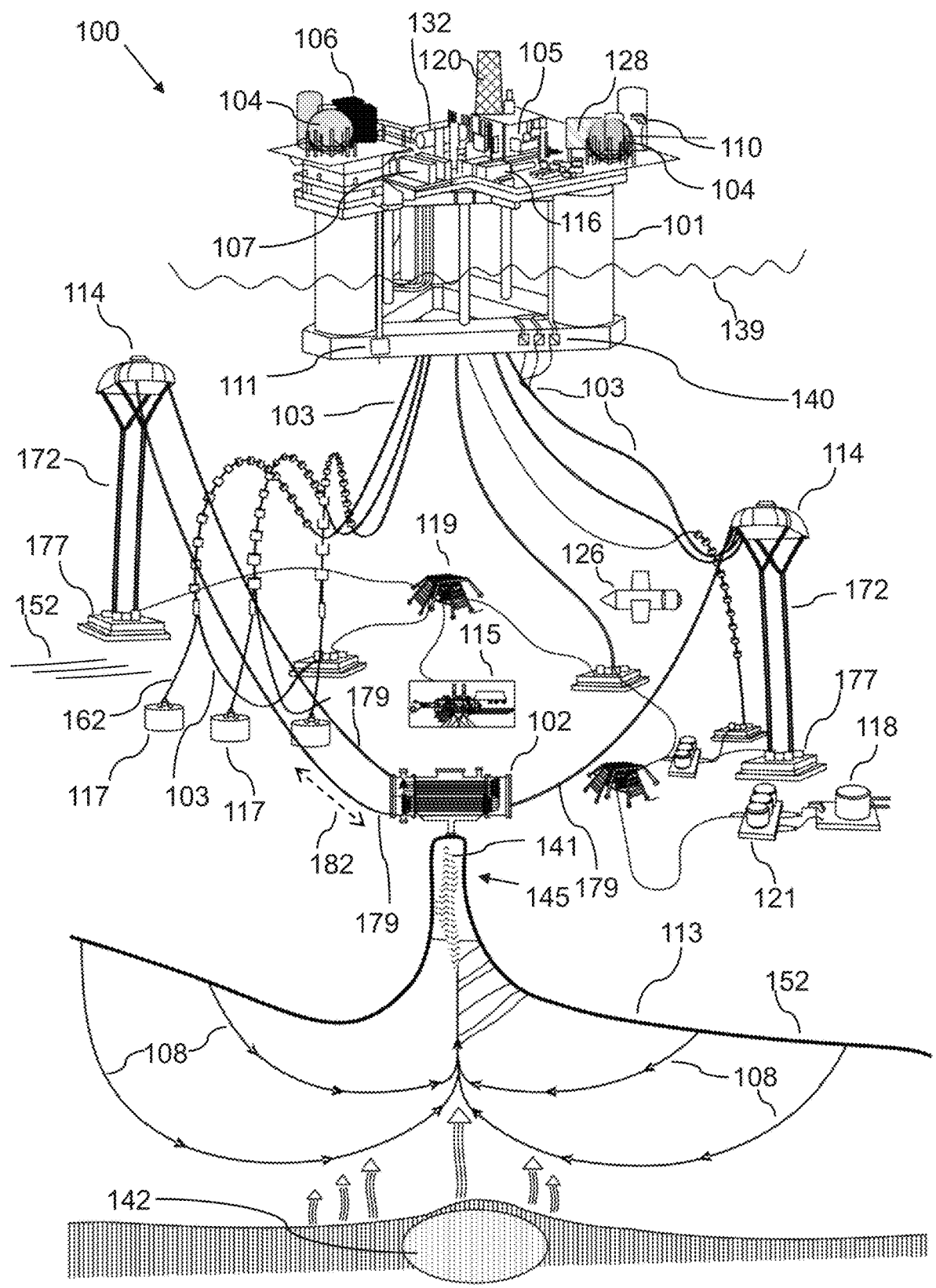
FIG. 1 is a schematic diagram illustrating a carbon negative clean fuel production system, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a carbon negative clean fuel production system 100 with reference to FIG. 1, in such manner that like reference numerals refer to like components throughout; a convention that we shall employ for the remainder of this specification.

In various embodiments, a carbon negative clean fuel production system 100 can include a set of components working together to form a complex unified whole, with a set of methods, procedures, and routines to carry out specific activities, such that the individual components and unique systems of component in this system 100 are referred to in the generic as system objects. Whenever appropriate in this document, terms in the singular form shall include the plural (and vice versa) when the terms elements, compounds, chemicals and minerals are used with a lower-case initial letter, the terms are used interchangeably. When the first letter of the term is uppercase, it is specifically referring to that term.

In various embodiments, the carbon negative clean fuel production system 100 provides a practical means for collecting heat from hydrothermal vents without dredging or even contact with the biodiverse area in the immediate vicinity of the hydrothermal vents and without transporting hydrothermal vent fluid to the surface or use of convection currents to turn generators.

There has been interest in finding a new fuel to replace oil for some time. many candidates have been proposed, from corn to solar, one of the most promising new fuels is silane, a fuel made from the silicon found in sand.

Silane is a gas at room temperature, which decomposes at relatively low temperatures and pressures to liberate hydrogen and deposit high purity silicon's. Silane is flammable and pyrophoric (i.e., ignites spontaneously when exposed to air). It is also considered an excellent hydrogen carrier. However, the biggest hurdle in using silane as a fuel replacement is that the production process uses almost as much energy as the resulting fuel produces.

Given that these fuels are currently produced using the energy from carbon-based fuels, they are not truly "renewable" or even carbon neutral. The carbon negative clean fuel production system 100 makes silane viable candidates to replace carbon-based fuels, by using the energy of a hydrothermal vent and its associated resources to produce silane and other industrial chemicals.

The carbon negative clean fuel production system 100 is carbon negative in its operation. The combustion of silane is a carbon neutral reaction, making the net result of the entire process carbon negative. Meaning it eliminates more carbon/$CO_2$ from the environment than it produces.

In various related embodiments, the number of vents along the Mid-Atlantic Ridge and their proximity to each other implies a high likelihood of interconnectivity of the systems 100 proposed herein, which can eventually form a network of energy systems 100 whose power is supplied by hydrothermal vents. Above these systems will sit numerous platforms manufacturing industrial chemicals and alternative fuels. As the number of platforms grow, the number of support staff will also grow eventually forming floating cities with all the infrastructure and conveniences associated with a major city all powered by the hydrothermal vent energy below the city.

The system 100 disclosed herein provides the first disclosed carbon negative method for harnessing this vast and inexhaustible natural source of energy, as a means of creating alternative fuels namely silanes and hydrides, with the additional benefit of producing formates of the alkali metal family from atmospheric $CO_2$. Formates can be formed by combining group 1 or group 2 alkali metals with hydrogen and $CO_2$. Formates have a variety of uses depending on which alkali metal it contains. Potassium formate is used as an environmentally friendly deicing salt for use on roads. Calcium formate is used as an animal feed preservative. All these alkali metals can be made into volatile hydrides sourced from the minerals extracted from seawater and the mineral separator.

In various embodiments, the carbon negative clean fuel production system 100 provides practical means of extracting resources, including minerals and heat, directly from hydrothermal vent fluid in close proximity to the vent itself, while minimizing the impact on the diverse biological ecosystem. The system is interconnected via two primary systems to create a positive energy feedback loop. An underwater electric grid and a sophisticated heat distribution network provides energy to devices connected to the system which in turn provide beneficial services or capabilities to the grid and heat distribution system supplying energy when, where, and in the form, it is needed.

In a related embodiment, a system control unit 121 monitors, regulates, measures and reports the flow of energy throughout the carbon negative clean fuel production system 100, while also monitoring environmental conditions; all of which help to maximize efficiency, while reducing the chance of system failures due to the harsh environmental conditions, the system control unit 121 acts as a data collection and distribution point for system, environmental and operational data.

In a related embodiment, a list of components (also referred to as system objects) of the carbon negative clean fuel production system 100 can include:

a) A platform 101;
b) A heat collection device 102;
c) A heat distribution system 103;
d) A chemical storage tank 104;
e) A control system 105;
f) A carbon dioxide removal system 106;
g) A water splitter 107;
h) A bunker station 110;
i) A seawater intake 111;
j) An internal fluid current 212;
k) A production float 114;
l) A mineral separator 115;
m) A seawater filtration unit 116;
n) An anchor platform 117;
o) A heat-driven electric generator 118;
p) An energy distribution controller 119;
q) A chemical production system 120;
r) A system control unit 121;
s) A pump 222;
t) A vent fluid inlet 223;
u) A cold water conduit 224;
v) A settling chamber 225;
w) An underwater vehicle 126;
x) A sand refinery machine 128;
y) Riffles 228;
z) An outlet valve 230;
aa) An exit hood 231;
bb) A cold water intake pump 232;
cc) A mineral extraction unit 233;
dd) A collection tray 234;
ee) An electromagnet 236;
ff) A coagulant injector 237;
gg) A sea level 139;
hh) energy distribution system connectors 140; and
ii) A precipitant 243.

As shown in the FIG. 1, the structure of a hydrothermal vent 145 can include:

a) A recharge zone 108;
b) A diffuse zone 113;
c) Hydrothermal emissions 141, typically in the form of a hot focused flow 141; and
d) A magma chamber 142.

In an embodiment, the carbon negative clean fuel production system 100 can include:

a) A platform 101, which includes a level surface on which people may stand and components may be positioned. The platform can float on a surface of the ocean or can in some alternative embodiments, be semi-submersible, submerged in the water column, or be located on the seafloor;
b) At least one anchor platform 117, for securing the platform 101 such that the anchor platform 117 tethers the platform 101 to the seafloor 152 using an anchor cable 162 in combination with winches and buoyancy controls 114 (production floats 114);

c) At least one production float 114, which can be used to lift anchor cables and other system objects that are suspended under water.

Production floats 114 can also function as key integration points influencing other system objects and feeding information systems with the data for a variety of system monitoring, optimizing and financial purposes while reducing the chance of system failures due to the harsh environmental conditions.

A production float can be a regulated buoyant device tethered to an anchor platform 117 via a fixed connection point or winch. Other system objects can be attached to a production float, its anchor platform or its tethers. The height of a production float may be altered by regulating its buoyancy or the length of its tethers.

Generally, the terms controlled and regulated are used interchangeably herein. However, as a general application, regulated has more of an individual device context while controlled is more of a broader system wide context. For example: That the regulator is controlled means that the regulator has the ability to control the flow of resources or limits a function, but its functions and sensors are connected to a master controller which directs the actions of the regulator;

d) A heat collection device 102, which is configured to capture heat emitted with hot water or emissions from a hydrothermal vent on the ocean floor. The heat collection device 102 can be any device capable of absorbing/capturing heat, such as a heat exchanger 102 or heat pump 102; The heat collection device 102 can include:
  i. an emissions intake 604, which can be funnel-shaped, for collecting (i.e., functioning as a suction intake for) the hydrothermal emissions 141;

e) A heat distribution system 103, which comprises a hose 103 (or pipe 103) or a plurality of hoses/pipes 103 for transporting a heat absorbing material, that can be a liquid or gas that can absorb heat and circulate through the hoses. The hoses 103 can be insulated and can be partially buried in the seafloor;

f) At least one energy distribution controller 119, which can be mounted between hose segments to regulate flow of the heat absorbing material, including regulating flow rate and direction to system objects;

g) A sand refinery machine 128, which is configured to refine sand into its chemical components, including silicon and oxygen. The sand can be transported in from other locations, can be dredged from a bottom of the ocean, or can in some cases be extracted from emissions of the hydrothermal vent.

The sand refinery machine 128 can use well-known methods of carbothermal reduction, such that the sand refinery machine 128 can be an electric arc furnace 128, which is configured to perform a carbothermal reduction with the sand and a coke compound, wherein the coke compound can be derived from coal or petroleum, or can be derived from a hydrocarbon produced from carbon dioxide and hydrogen, using the electric energy, all produced in the system 100.

Alternatively, the sand refinery machine 128 can use other well-known reduction processes to produce silicon and oxygen from sand, including the process defined in China Patent No. CN1081164C;

h) A control system 105, which includes sensors, transmitters, meters, receivers, switches, computers, motors, valves, pumps, and other components that monitors, manage, command, direct, and regulates the behavior of other system objects. When the term regulated or any of its forms are used in this document, it means the system object is under the control of one or more control systems and detailed data is being collected about every aspect of its operation;

i) Optionally an underwater vehicle 126, which can be tethered or autonomous, and can be employed for inspecting and/or repairing submerged parts of the system;

j) A mineral separator 115, also called a mineral sluice box 115 or mineral separator 115, is a box, trough or the like, with riffles 228 on the inner bottom 250, into which mineral rich hydrothermal vent fluid is directed and mixed with cooler surrounding ocean water (injected via pump 237) or other coagulants to separate from the vent fluid, through coagulation and precipitation 243, such that minerals and other materials are deposited in the riffles 228;

k) A chemical storage tank 104;

l) A Carbon dioxide removal system 106, which is configured to remove carbon dioxide from the atmosphere and from the waste/emissions of system objects. Byproducts of this step vary based on the method used to remove the carbon dioxide from the atmospheric gases. Some potential processes, such as disclosed in U.S. Pat. No. 4,568,522A, result in carbonates and halogens. A halogen of carbon is often called synfuel or synthetic fuel. The Sabatier process reacts hydrogen with carbon dioxide, such as disclosed in U.S. Pat. No. 3,488,401 to produce methane and water. Other processes result in formates, such as disclosed in U.S. Pat. No. 9,255,057B2. A complimentary process to the formation of silane would use silicon from the sand refinery process to form silicon carbide;

m) A water filtration device 116, which is configured to remove minerals and pollutants from seawater;

n) A positioning system, which can be a regulated, integrated set of production floats, winches, motors, gyroscopes, and other system objects from which the heat collection device and other system objects are attached or tethered, such that manipulation of the winches and float buoyancy can move the system objects in any of the three-dimensional x, y or z coordinates for optimal placement and integration within the system;

o) A heat-driven electric generator 118, which can be configured as a Stirling generator 118, which can include a Stirling engine connected to an electric generation device (generator), such that the Stirling generator is configured to generate electricity from heat of the heat absorbing material;

p) A bunker station 110, which can be an alternative fuel offloading station which includes valves, elbows, dispensing equipment, pressure gauges, measuring and payment systems. A bunker station 110 may be located on any type of platform on the water or be subsurface;

q) A water splitting device 107, which is configured to use electric power generated by the Stirling generator to split water into hydrogen and oxygen. The water splitting device can use any of various well-known methods and devices for water splitting, including such methods and devices as disclosed in U.S. Pat. Nos. 6,726,893 and 4,394,230, both of which are incorporated herein by reference in their entirety;

r) A system control unit 121, which is a regulated device that controls, measures and reports the resources transferred to and from system objects;
s) A chemical production system 120, which uses the silicon and minerals produced in the system to produce Hydrides, Halides and Silane; and
t) A flow controller, which can be configured to control the flow of vent fluid onto and around the heat collection device 102.

In a related embodiment, as shown in FIG. 7, the system control unit 121 can include:
a) A processor 702;
b) A non-transitory memory 704;
c) An input/output 706; and
d) A system manager 710, which is configured to control system objects in communication via a network, which can be wired and/or wireless; all connected via
e) A data bus 720.

In related embodiments, in addition to the main system control unit 121, system objects in the carbon negative clean fuel production system 100 can have local controllers, such as embedded microcontrollers, and a plurality of local sensors in order to control/regulate local operation of the system object, which can include the heat collection device 102, production floats 114, the seawater filtration unit 116, the heat-driven electric generator 118, the mineral extraction unit 233, the cold water intake pump 232, etc.

In a related embodiment, as shown in FIGS. 1, 4, 5, and 6A the process 400, 500 begins with external energy being supplied 444 to the electric grid 300 from a platform to start circulation of a working substance through the energy distribution system 300, which can be configured to distribute both electric energy and heated working fluid 619. The energy distribution controllers 119 and system control units 121 are controlled to allow heated working fluid 619 to reach the system objects in quantities and temperatures appropriate for each system object. As the heat absorbing material warms, its heat is transferred to platforms with heat-driven electric generators which in turn provide additional electricity to the electric grid allowing the initial source of electricity to shut down. At this point the heat distribution system and electric grid are self-sustaining through a regulated positive feedback loop.

In a further related embodiment, once the electric grid and heat transfer system have obtained positive feedback state, additional systems can be started. The floating platform will begin filtering seawater to reach ideal chemical composition while the sand refinery 128 and water splitters 107 reach their operating temperatures. The products from these systems are input to the carbon dioxide removal system 106 where formates and carbonates are produced and to the chemical production system 120 where hydrides, halides and silane are produced.

In a related embodiment, FIG. 1 Illustrates a basic implementation of the carbon negative clean fuel production system 100. For simplicity of description, we will refer to fuel production capabilities as taking place on a single semi-submersible platform. an electric grid and a thermal transfer system 103 function as integrating interfaces occurring in subsea locations and connecting 140 to platforms as needed. Stirling generators are employed due to their innate ability to take advantage of differences in temperature and pressure extremes. However, there are other heat engine types that can be used to generate electricity using heat in a deep-water location, although relative efficiency would likely be substantially less.

In a further related embodiment, the sand method of silane production can be used due to its long-proven history of effective silane production. Newer methods of silane production are available and may be considered for individual installations as their safety and efficiencies are proven. Implementations may use platforms on or below the water surface, for example as needed to accommodate capacity or geologic/biologic conditions and goals. There may also be safety reasons to separate function onto different platforms. The potential for explosive silane incidents is just one of many safety issues that could make multiple platforms desirable.

In a related embodiment, the semi-submersible production platform 101 can be of a size capable of supporting the equipment and other resource needs including connections to the electric grid, the heat distribution system, the sand processing plant and the alternative fuel refinery. The platform 101 includes the control system 105 that monitors and regulates the entire carbon negative clean fuel production system 100.

In another related embodiment, the carbon removal system 106 can be configured to use the Sammels process, as described in PCT/International Patent Application number WO2014202855A1 and U.S. Pat. No. 4,673,473, both of which are hereby incorporated herein by reference in their entirety, to produce valuable formate chemicals based on input chemicals provided by the recovery of minerals from the mineral separator 115 and the seawater surrounding the platform, such that energy is sourced from the hydrothermal vent through connections with the heat distribution system and integrated electric grid Processes for isolation of minerals from seawater and further separation of the minerals into the base elements such as alkali metals are well documented, and many options exist. In a related embodiment, the carbon negative clean fuel production system 100 can use the Cunningham process, as described in U.S. Pat. No. 2,867,568, which is hereby incorporated herein by reference in its entirety; because the Cunningham process combines the separation of alkali metals with the creation of hydrides in one step. The primary drawback of this Cunningham process is the amount of energy consumption. In a land-based carbon fuel environment, this fuel consumption would make the process uneconomical and very carbon positive. However, by using the energy from a hydrothermal vent, this process is able to produce industrial quantities of hydrides economically, with no carbon footprint.

In another related embodiment, the carbon negative clean fuel production system 100 can include a seawater filtration unit 116 which is configured to filtrate surrounding ocean water, such that a primary output includes water for input to a water splitting process and the filtered-out brine In yet another related embodiment, the carbon negative clean fuel production system 100 can include a chemical production system 120, which takes as input chemicals from previously described systems to produce silane, halides, and hydrides. Silane produced can include dislane and trislane. Halides can include fluoride, chloride, bromide, iodide, astatide. Hydrides can include hydrogen compounds, binary metal hydrides, ternary metal hydrides, coordination complexes, and cluster hydrides. The chemical production system 120 can be configured to use well-known processes for production of organosilicon compounds, including the "direct process", also called the Direct Synthesis, Rochow Process, and Müller-Rochow Process, including copper-catalyzed reactions of alkyl halides with silicon, which take place in a fluidized bed reactor. Silane can be produced in a two-step process wherein 1) silicon is treated with hydrogen chloride at about 300° C. to produce trichlorosilane and hydrogen gas; and 2) trichlorosilane is converted to a mixture of silane and silicon tetrachloride in a redistribution reaction requiring a catalyst.

In a further related embodiment, the chemical production system 120 can be configured to use any of various well-known methods and devices for production of Silane, including such methods and devices as disclosed in U.S. Pat. Nos. 4,601,798, 4,499,063, CA Patent No. 2357025, European Patent No. 1558520B1, China Patent No. 1938220; all of which are hereby incorporated herein by reference in their entirety.

In a further related embodiment, the chemical production system 120 can be configured to use any of various well-known methods and devices for production of Halides, including such methods and devices as disclosed in CA2234688A1 and U.S. Pat. No. 3,644,220 A; both of which are hereby incorporated herein by reference in their entirety.

In a further related embodiment, the chemical production system 120 can be configured to use any of various well-known methods and devices for production of biodiesel, including such methods and devices as disclosed in U.S. Pat. No. 7,638,314 B2; which is hereby incorporated herein by reference in its entirety.

In another further related embodiment, the chemical production system 120 can be configured to react metals of the solid minerals, including sodium or potassium, with hydrogen under a high pressure and a high temperature to produce hydrides, which are metal hydrides with the chemical composition mH, where m is the metal and H is hydrogen; such as described in PCT International Patent Application No. WO2012114229A1, which is hereby incorporated herein by reference in its entirety.

In a related embodiment, the chemical production system 120 can be configured to react the silicon with hydrogen under a high pressure and a high temperature to produce silane.

In a related embodiment, the chemical production system 120 can be configured to react to react metals of the solid minerals with halogens under a high pressure and a high temperature to produce halides, wherein the halogens can be extracted from the seawater, for example as a solute output from solutes produced by the seawater filtration unit 116.

In a yet further related embodiment, the high pressure can be in a range of 5-200 bar, or at least 5 bars, and the high temperature can be in a range of 300-400 degrees Fahrenheit, or 200-500 degrees Fahrenheit, or at least 200 degrees Fahrenheit.

In another related embodiment, the water splitting system 107 can be configured to split water via a process of electrolysis using the surrounding ocean water as its primary input. However, thermolysis or other water separating techniques can alternatively be used and are viable due to the almost unrestricted availability of energy from the electric grid and heat distribution sourced from the hydrothermal vent through connections to the integrated electric grid and energy distribution systems. The water splitting system 107 can provide the hydrogen and oxygen to the chemical processing system for producing silane, hydrides, and halides.

In another related embodiment, the chemical production system 120 can use input material/chemicals provided by:
a) minerals 656 from reverse osmosis of seawater provided by the seawater filtration unit 116;
b) hydrogen and oxygen from splitting of filtered water seawater provided by the water splitting system 107; and/or
c) Minerals from processing of the hydrothermal vent fluid provided by the mineral separator 115.

In another related embodiment, the chemical production system 120 can be configured to compress hydrogen in the presence of other chemicals at a temperature in a range of 300-400 degrees Fahrenheit to form hydrides.

Figure 2A:
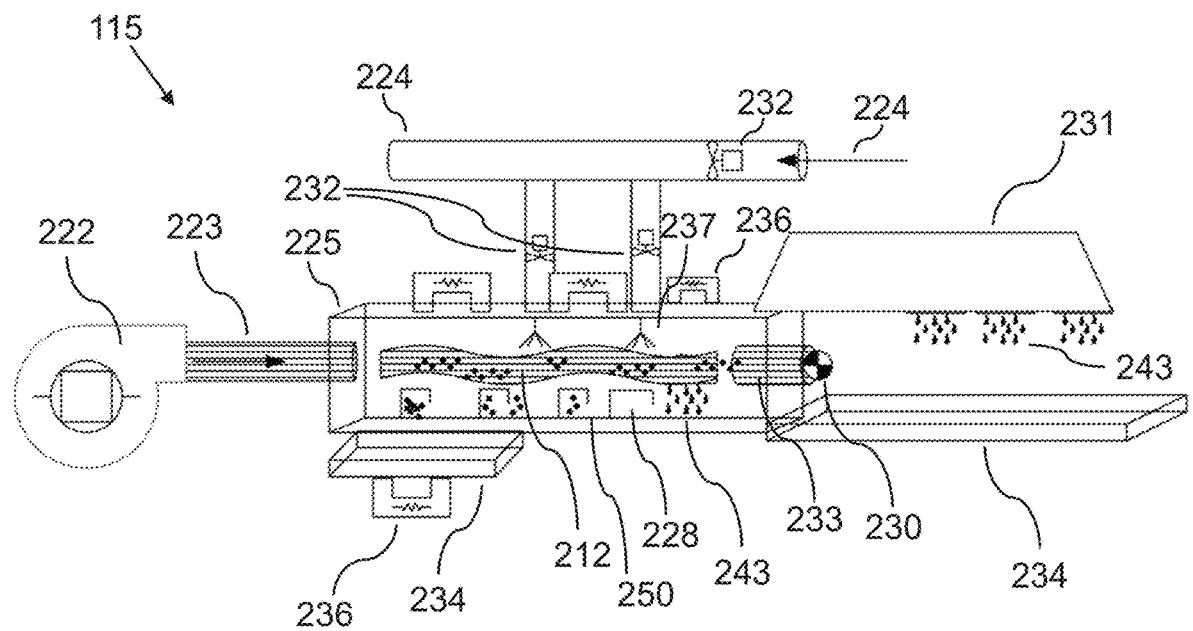
FIG. 2A is a schematic diagram illustrating a mineral separator, according to an embodiment of the invention.
Figure 3:
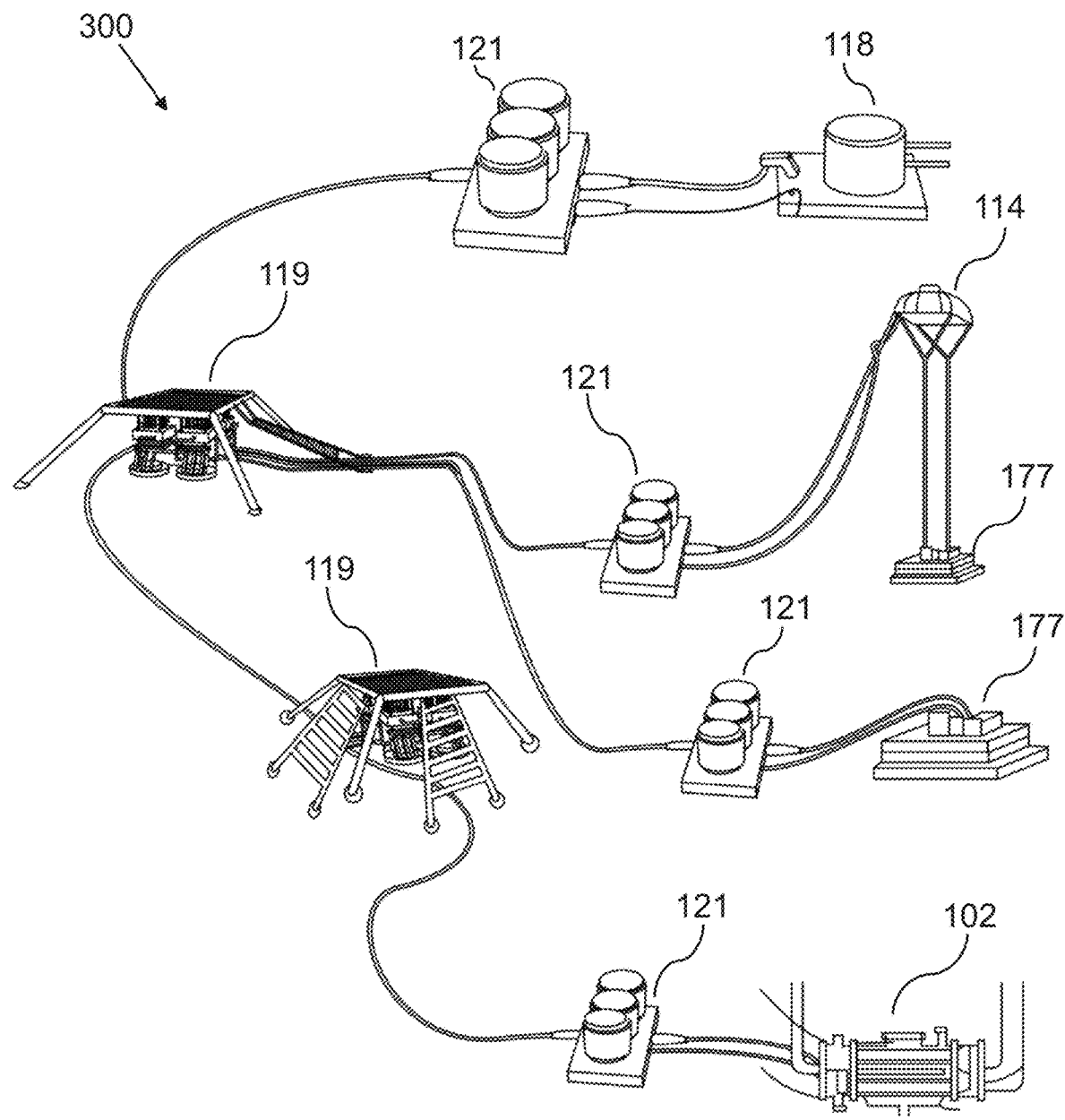
FIG. 3 is a schematic diagram illustrating a part of the carbon negative clean fuel production system, according to an embodiment of the invention.

In related embodiments, FIG. 1 shows the general placement of system objects, including the mineral separator 115. FIG. 2A shows more detail of components of the mineral separator 115. FIG. 3 shows the major system objects that provide the energy distribution system, which provides both heat distribution as well as electric grid operations.

Figure 2B:
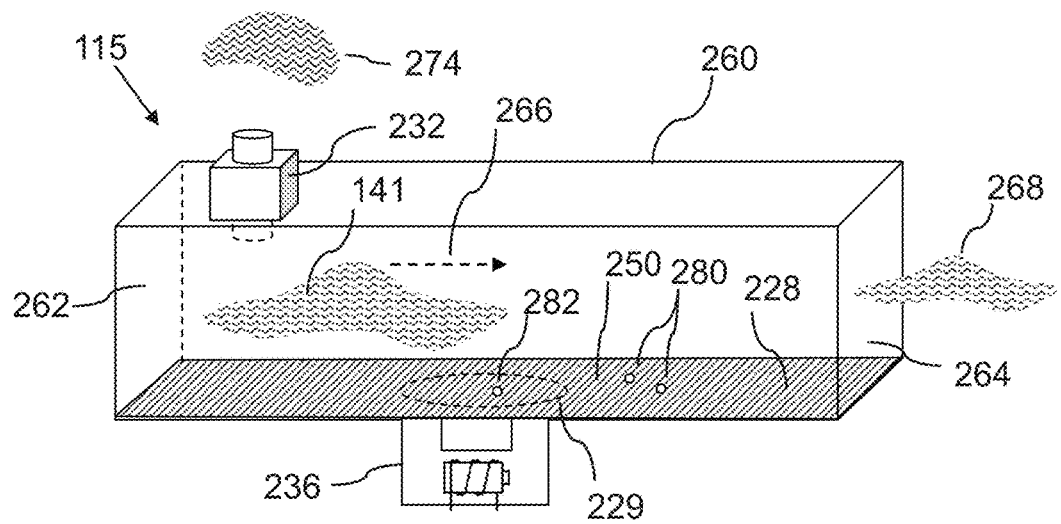
FIG. 2B is a schematic diagram illustrating a mineral separator, according to an embodiment of the invention.
Figure 4:
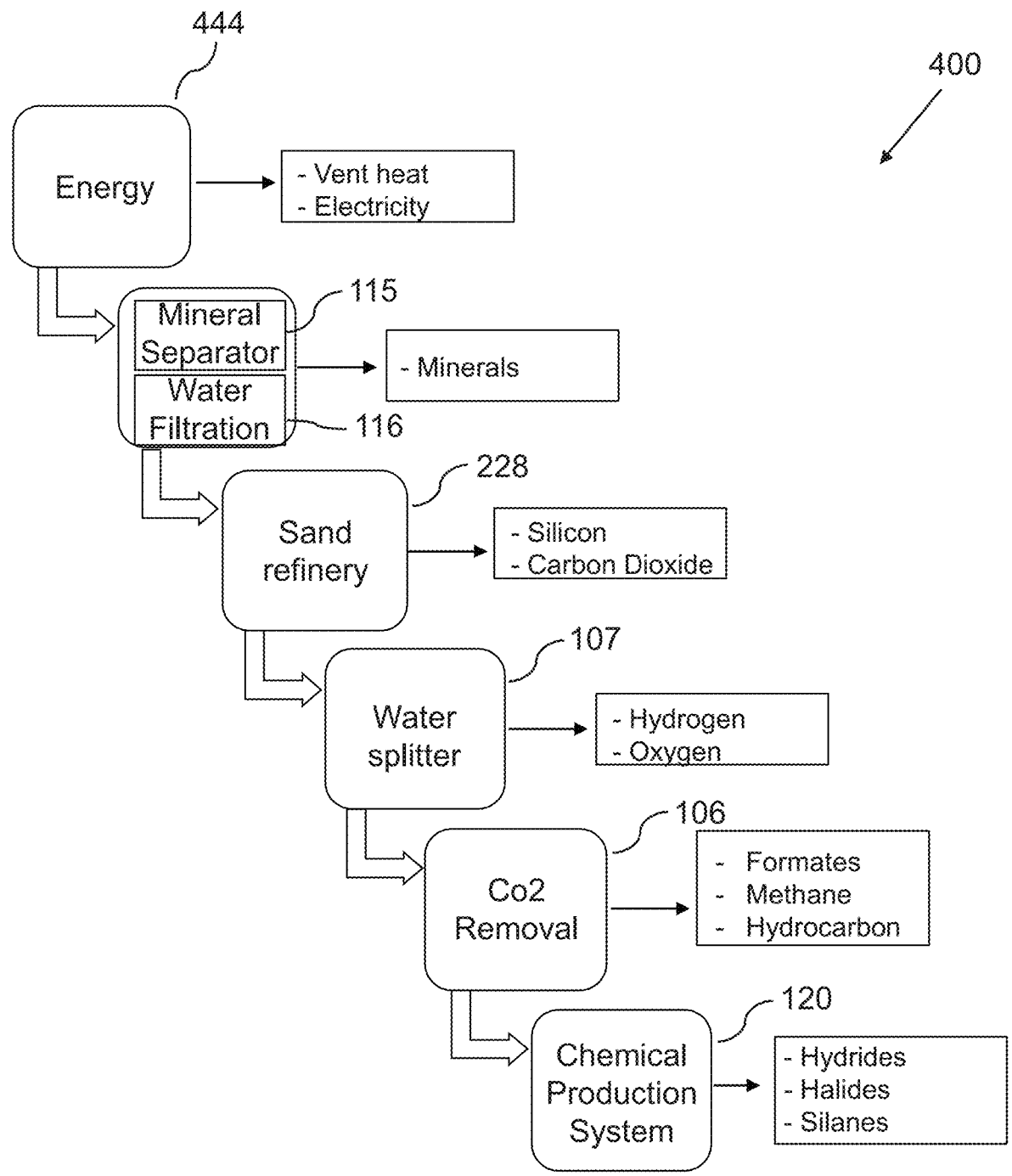
FIG. 4 is a schematic diagram illustrating system flow of the carbon negative clean fuel production system, according to an embodiment of the invention.
Figure 5:
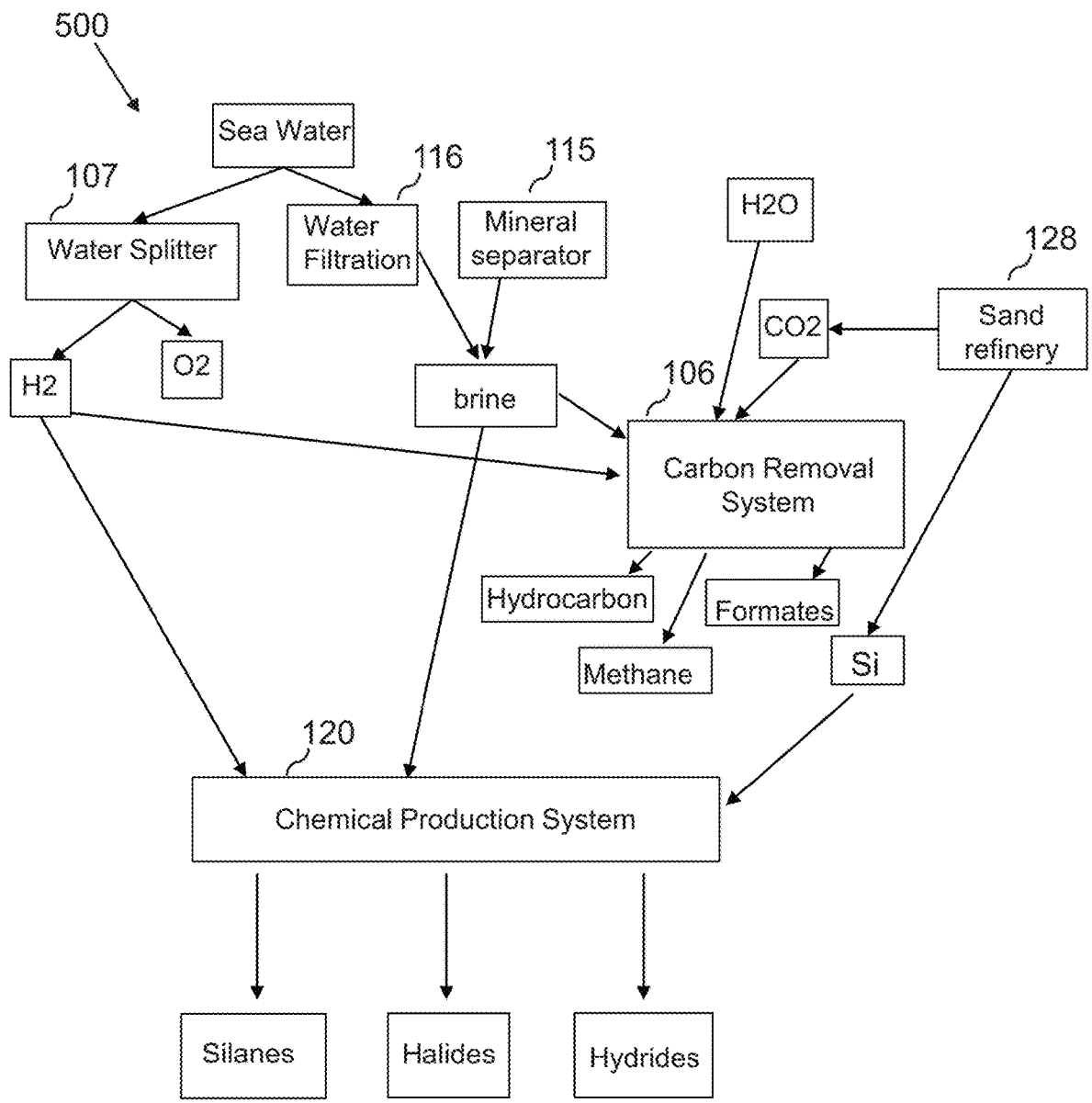
FIG. 5 is a schematic diagram illustrating system flow of the carbon negative clean fuel production system, according to an embodiment of the invention.

In a related embodiment, FIGS. 2A, 2B, and 4 shows a system flow of the carbon negative clean fuel production system 100, including:
a) the use of hydrothermal vent energy in both thermal and electrical forms;
b) incorporating the minerals extracted from the mineral separator 115 and water splitting with a parallel process of refining sand into its core elements, the required chemicals from the prior steps providing the materials necessary for the carbon-dioxide removal process;
c) A regulated variable speed pump 222 moves the superheated mineral rich vent fluids through the inlet pipe 223 into the settling chamber 225 where it is mixed with the surrounding colder ocean water via a cold water conduit 224 under pressure from a coagulant pump 232. Mixing of hot and cold water cools the chamber fluids below the melting or boiling point of some of the minerals in the vent fluid smoke facilitating coagulation and precipitation via the coagulant injector 237;
d) A regulated cold water pressure pump 232 injects the right amount of cold water or coagulant into the settling chamber 225 where riffles 228 catch the heavier precipitating materials separating them from lighter dissolved minerals. The exit valve 130 controls the fluid flow rate to avoid a fast internal chamber current 112 that washes out the desired minerals. A current of the proper speed and temperature provides time for the minerals to congeal, coagulate, solidify, and precipitate 243;
e) The solidifying, coagulating minerals precipitate 243 into the collection tray. The tray simplifies the collection of precipitated minerals 243. The collection trays will have a woven mat of suitable material in the bottom to grab and hold the precipitates reducing mineral loss as current flows over the trays and as they are manipulated and returned to the surface; and
f) The regulated polarity reversible, variable strength electromagnets 236 facilitate mineral precipitation by their magnetic properties.

In a related embodiment, a carbon negative clean fuel production system 100 for the production of alternative fuels and industrial chemicals using the energy and resources from a hydrothermal vent, the system comprising a set of system objects as described above, can include:
a) means for distributing a working substance heated by a hydrothermal vent to a variety of system objects producing alternative fuels and industrial chemicals;
b) means for delivery of the working substance from the heat collector to a platform where the heat is consumed;

c) means for converting at least a portion of the heat contained in the working substance to a second form of energy at an underwater platform;
d) means of collecting seawater from the area around a platform using the energy produced;
e) means of using the energy to refine sand into silicon and oxygen or chemicals that may be present in the sand using the energy produced;
f) means of extracting chemicals from the seawater using the energy produced;
g) means for combining hydrothermal vent minerals chemicals into clean fuels;
h) means for removing more carbon dioxide from the atmosphere than is produced by the carbon negative clean fuel production system 100;
i) means for precipitating minerals and chemicals from the hydrothermal vent fluid without bringing the fluid to the surface;
j) means for utilizing the heat contained in the working substance and the cold water from the surrounding environment to drive a Stirling engine;
k) means of separating industrial chemicals from seawater using the heat or subsequent energy form derived from the heat of a hydrothermal vent; and
l) means of combining hydrogen with the minerals to form hydrides.

In a related embodiment, the carbon negative clean fuel production system 100 can be used for recovery of resources contained in a hydrothermal fluid exiting a hydrothermal vent.

In another related embodiment, the carbon negative clean fuel production system 100 can include production of formates using the minerals and energy extracted from a hydrothermal vent.

In yet another related embodiment, the carbon negative clean fuel production system 100 can include production of silane using the minerals and energy extracted from a hydrothermal vent.

In a related embodiment, the carbon negative clean fuel production system 100 can include production of hydrides from the minerals and energy extracted from a hydrothermal vent.

In a related embodiment, the carbon negative clean fuel production system 100 can include production of halides from the minerals and energy extracted from a hydrothermal vent.

In a related embodiment, the carbon negative clean fuel production system 100 can include removal of atmospheric and or industrial process carbon dioxide using the minerals and energy extracted from a hydrothermal vent.

In a related embodiment, the carbon negative clean fuel production system 100 can include production of silicon from any source materials using the minerals and energy extracted from a hydrothermal vent.

In a related embodiment, the carbon negative clean fuel production system 100 can include a system and method of a regulated heat collecting device transferring the heat of a hydrothermal vent into a regulated thermal transfer system.

In a related embodiment, the carbon negative clean fuel production system 100 can include a system and method of using the energy of a hydrothermal vent to power a Stirling engine.

In a related embodiment, the carbon negative clean fuel production system 100 can include the use of magnetism in the separation of minerals from hydrothermal vent fluid, using a mineral separator 115.

In a related embodiment, the carbon negative clean fuel production system 100 can include system and method of using a production float 114 to position a system object device within a system collecting resources from a hydrothermal vent.

In a related embodiment, the carbon negative clean fuel production system 100 can include a system and method of using a mineral separator 115 or settling tank to extract minerals from vent fluid.

In a related embodiment, the carbon negative clean fuel production system 100 can include a system and method of using a regulated device with riffles 228 in the recovery of minerals from a hydrothermal vent.

In a related embodiment, the carbon negative clean fuel production system 100 can include a system and method of placing a mineral separator 115 over a hydrothermal vent to collect the minerals from vent fluid.

In a related embodiment, the carbon negative clean fuel production system 100 can include a system and method of regulating energy usage from an underwater electric grid and thermal distribution system where the energy is sourced from a hydrothermal vent.

In a related embodiment, the carbon negative clean fuel production system 100 can include use of an exit hood 231 to finalize sedimentation by capturing and cooling residual warm vent fluid exiting a mineral separator 115.

In a related embodiment, the carbon negative clean fuel production system 100 can include a system and method of creating a positive energy feedback loop in the collection and distribution of energy from a hydrothermal vent.

In a related embodiment, the carbon negative clean fuel production system 100 can include creation of silicon carbide in a carbon sequestration process using the energy and resources of a hydrothermal vent.

In a related embodiment, the carbon negative clean fuel production system 100 can include a sea level platform 101 with support for a human presence, such the platform 101 can include conventional human support systems including bathrooms, kitchens, entertainment and waste disposal to avoid polluting the ocean.

In a further related embodiment, the carbon negative clean fuel production system 100 can further include a recycling system, such that the energy available from a hydrothermal vent can be used for the recycling system, which can recycle papers, metals, plastics and other trash collected from the ocean. The recycling system can be configured as a large surface skimmer connected to a recycling plant mounted on the platform 101. As litter is sucked into the skimmer, a lifting bucket line can transport the trash from the skimmer to a conveyer where the trash can be shredded, sorted and processed into useable products.

Figure 6A:
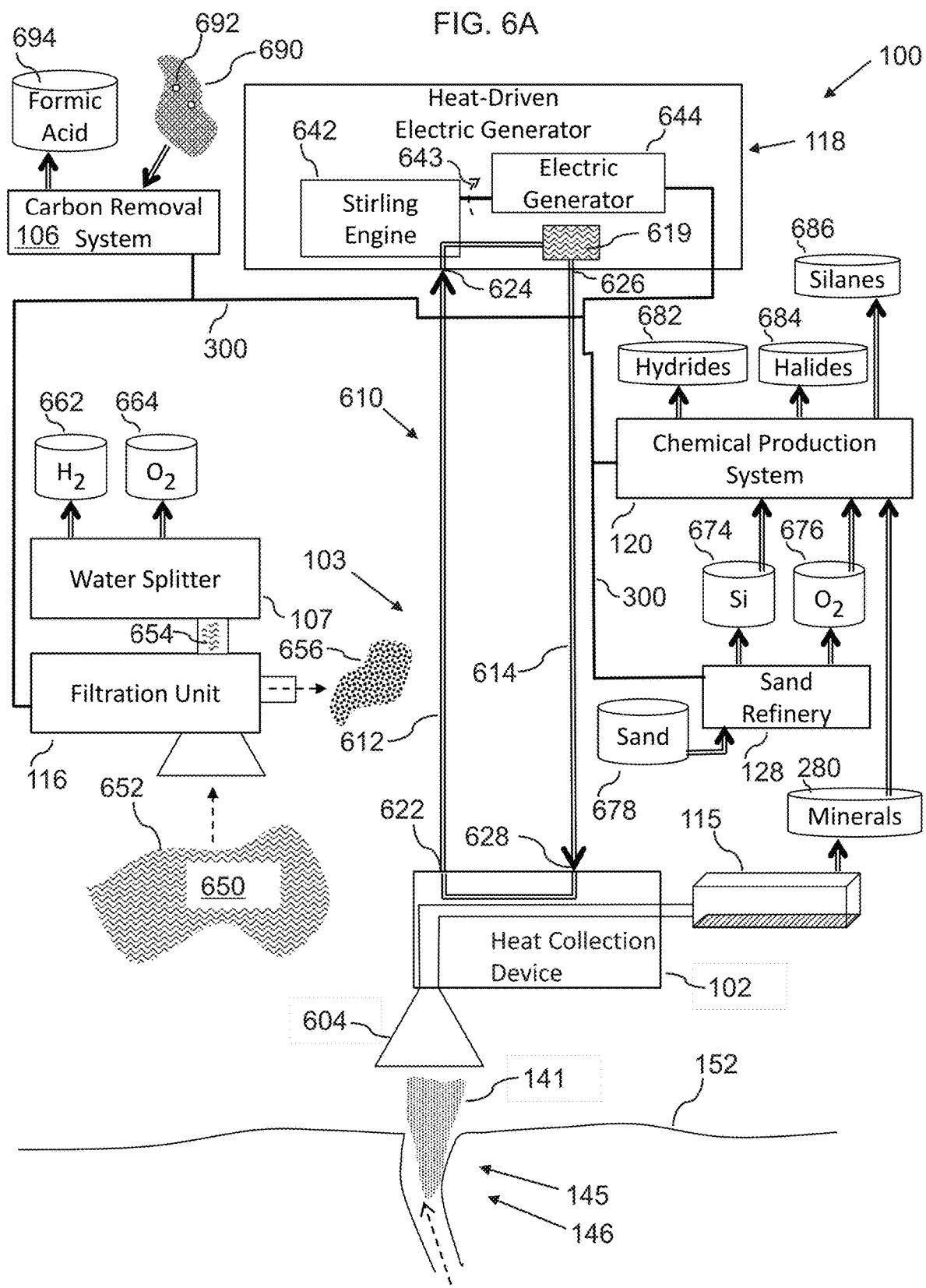
FIG. 6A is a schematic diagram illustrating a carbon negative clean fuel production system, according to an embodiment of the invention.

In an embodiment, as shown in FIGS. 1 and 6A, a carbon negative clean fuel production system 100 can include:
a) a main platform 101;
b) a heat collection device 102, which can be configured to capture heat from hydrothermal emissions 141 from a hydrothermal vent 145 on a floor 152 of an ocean 650, wherein the heat collection device 102 is configured to receive the hydrothermal emissions 141 from the hydrothermal vent 145, for example via an emissions intake 604 positioned adjacent to the hydrothermal vent 145 or via a direct pipe connection 613;
c) a heat-driven electric generator 118, which is configured to receive the heat from the hydrothermal vent 145 and produce electric energy, wherein the heat-driven electric generator 118 is mounted on a surface of the main platform 101; and d) a heat distribution system 103, comprising:
  i. a heat absorbing material 619; and
  ii. at least one heat transporting pipe 610, comprising:
    a heat transport segment 612; and
    a return flow segment 614;
      wherein a first end of the heat transport segment 612 is connected to a collection output 622 of the heat collection device 102 and a second end of the heat transport segment 612 is connected to a generator input 624 of the heat-driven electric generator 118; and
      wherein a first end of the return flow segment 614 is connected to a generator output 626 of the heat-driven electric generator 118 and a second end of the return flow segment 614 is connected to a collection input 628 of the heat collection device 102;
    such that the heat absorbing material 619 flows through the heat collection device 102, such that the heat absorbing material 619 absorbs the heat from the hydrothermal emissions 141; and
    such that the heat absorbing material 619 flows through the heat-driven electric generator 118, such that the heat-driven electric generator produces the electric energy from the heat of the heat absorbing material 619.

In related embodiments, as shown in FIGS. 1, 6A, 6B, 6C, a hydrothermal vent 145 can be:
  a) a natural hydrothermal vent 146, i.e., a hydrothermal vent on an opening in the ocean floor 152, wherein the natural hydrothermal vent 146 has been created by a natural geophysical process; or
  b) an engineered hydrothermal vent 647, which is a hydrothermal vent that is engineered to allow a direct pipe connection 613 from the engineered hydrothermal vent 647 to the heat collection device 102.

In a further related embodiment, an engineered hydrothermal vent 647 can be constructed ground-up in the seafloor, by drilling a pipeline 616 into the ocean floor 152, wherein the pipeline can be capped with a cap 617 at the level of the ocean floor 152, such that a direct pipe connection 613 can be connected between the cap 617 and the heat collection device 102.

In another further related embodiment, an engineered hydrothermal vent 647 can be constructed from a natural hydrothermal vent 146 that has been capped with a cap 617, such that a direct pipe connection 613 can be connected between the cap 617 and the heat collection device 102.

In a related embodiment, the carbon negative clean fuel production system 100, 602, 603 can further include:
  a direct pipe connection 613;
  wherein the hydrothermal vent 145 is an engineered hydrothermal vent 647;
  such that the direct pipe connection 613 is connected between the engineered hydrothermal vent 647 and the heat collection device 102, as shown in FIG. 6C, such that the heat collection device 102 receives the hydrothermal emissions 141 via the direct pipe connection 613.

Figure 6B:
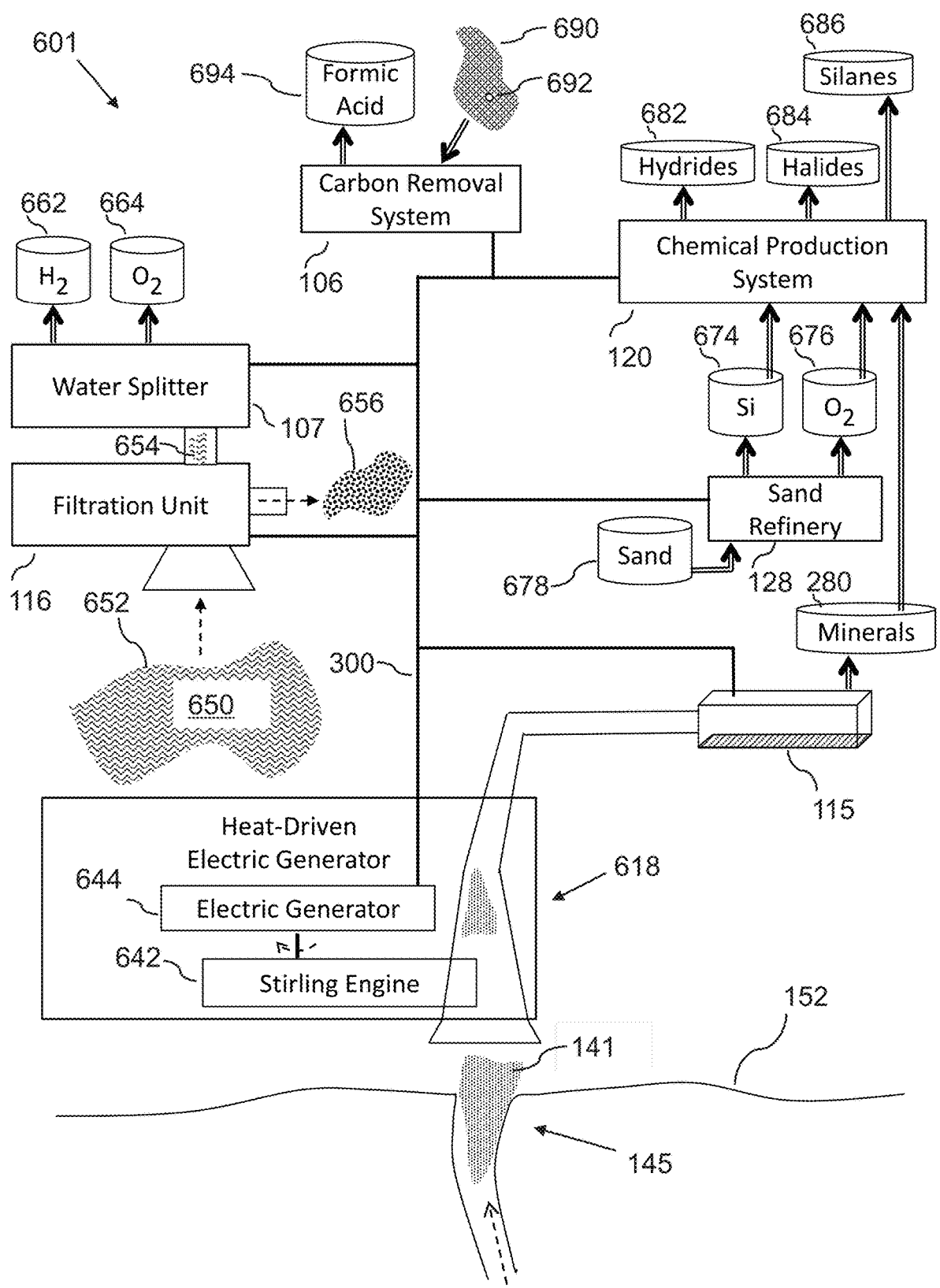
FIG. 6B is a schematic diagram illustrating a carbon negative clean fuel production system, according to an embodiment of the invention.
Figure 6D:
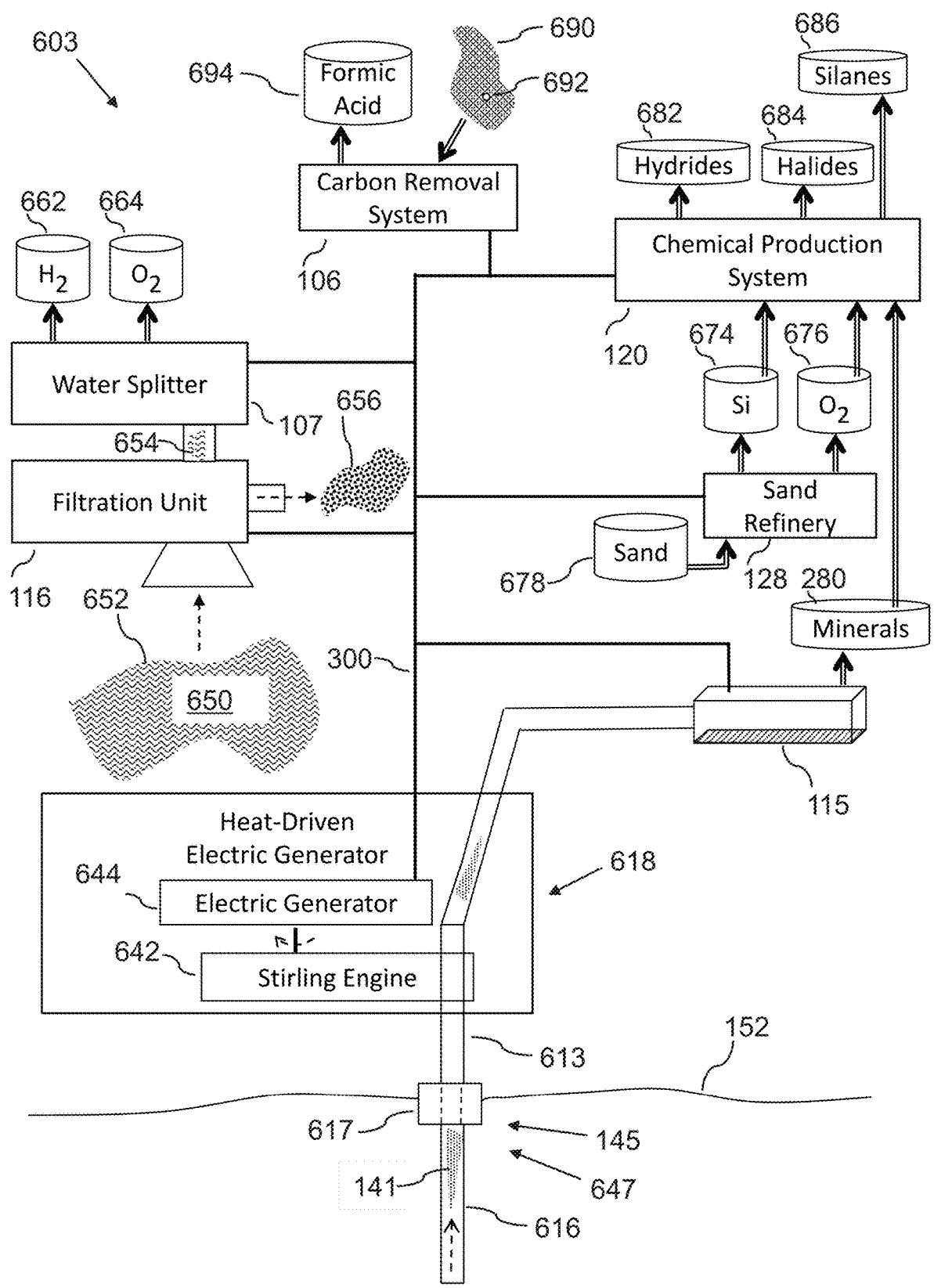
FIG. 6D is a schematic diagram illustrating a carbon negative clean fuel production system, according to an embodiment of the invention.

In an alternative related embodiment, the direct pipe connection 613 can be connected directly to the heat-driven electric generator 618, as shown in FIG. 6D, such that the direct pipe connection 613 is connected between the engineered hydrothermal vent 647 and the heat-driven electric generator 618, such that the heat-driven electric generator 618 receives the hydrothermal emissions 141 via the direct pipe connection 613.

In further related embodiments of the carbon negative clean fuel production system 603, as shown in FIG. 6C, wherein the direct pipe connection 613 is connected directly to the heat-driven electric generator 618, the heat-driven electric generator 618, can be positioned in relative proximity to the engineered hydrothermal vent 647 (i.e. for example adjacent to but separated by the direct pipe connection 613), below a surface of the ocean 650; or the heat-driven electric generator 618 can be positioned on an above surface platform 101, which can be a floating main platform 101.

In another related embodiment, the platform 101 can be configured to float on a surface of the ocean. Alternatively, the platform 101 can be submerged, submersible, land based, or positioned on a floor of the ocean.

In another related embodiment, the carbon negative clean fuel production system 100 can further include:
  a) at least one anchor platform 117; and
  b) at least one tether/anchor cable 162;
  wherein the anchor platform 117 can be configured to be positioned on a floor 152 of the ocean; and wherein a first end of the anchor cable 162 is connected to the platform 101 and a second end of the tether is connected to the platform 101;
  such that the platform 101 is secured in position.

In a related embodiment, the heat transporting pipe 610 can be an insulated pipe.

In another related embodiment, the heat absorbing material 619 can be a liquid 619.

In a further related embodiment, the liquid 619 can be a hydrofluorocarbon 619.

In yet another related embodiment, as shown in FIG. 6A, the heat-driven electric generator 118 can be a Stirling generator 118, which can include:
  a) a Stirling engine 642, which can be configured to generate rotational mechanical energy 643 from the heat of the heat absorbing material 619; and
  b) an electrical generator 644, which is configured to convert the rotational mechanical energy 643 into the electric energy 300.

In another related embodiment, as shown in FIGS. 1, 2A, 2B, and 6A, the carbon negative clean fuel production system 100 can further include:
  a mineral separator 115, which includes an enclosure 260 that can include riffles 228 along an inner bottom of the enclosure;
  wherein an input opening 262 of the enclosure 260 receives the hydrothermal emissions 141 from the hydrothermal vent, such that the hydrothermal emissions 141 pass through 266 the enclosure 260, such that solid minerals 280 are deposited in the mineral separator 115 (such as in the riffles 228) and remaining emissions 268 are ejected from an output opening 264 of the enclosure 260.

In further related embodiments, the mineral separator 115 can be constructed according to well-known methods for design of mineral separators 115 for use above or below water, which can include sluice boxes with riffles and collector mats/carpets, or other mechanical separators, centrifugal separators, mesh separators, and other forms of mechanical, chemical, and electromechanical, and combined technology mineral separators, as for example commonly used in placer mining and other forms of mining.

In a further related embodiment, as shown in FIG. 2B, the mineral separator 115 can further include:
  at least one magnet 236, which is mounted below the riffles 228;

such that the at least one magnet causes magnetic minerals 282 to be deposited in a section 229 of the riffles 228 close to the at least one magnet 236.

In another further related embodiment, as shown in FIG. 2B, the mineral separator 115 can further include:

at least one pump 232, which is configured to pump cold seawater 274 into the enclosure 260, such that the cold seawater 274 cools, congeals, and sediments the hydrothermal emissions 141, whereby dissolved mineral parts 280 of the hydrothermal emissions 141 are coagulated and thereby are deposited in the riffles 228 as sedimented minerals 280.

In yet another related embodiment, the carbon negative clean fuel production system 100 can further include:

a seawater filtration unit 116, which is configured to filter seawater 652 from the ocean 650, for example by reverse osmosis, to produce filtered freshwater 654 and solutes 656 which include brine 656 and solute minerals 656.

In another related embodiment, the carbon negative clean fuel production system 100 can further include:

a water splitting device 107, which is configured to use the electric energy 300 generated by the heat-driven electric generator 118 to split the filtered freshwater 654 into hydrogen 662 and oxygen 664 by a process of electrolysis.

In yet another related embodiment, the carbon negative clean fuel production system 100 can further include:

at least one anchor tether 172;
at least one anchor structure 177;
at least one structural support cable 179; and
at least one production float 114, such that the at least one production float 114 is configured to be submerged, wherein the production float has a density less than seawater;
wherein the at least one anchor structure 177 is positioned on the floor 152 of the ocean;
wherein the at least one production float 114 is connected to the at least one anchor structure 177 via the at least one anchor tether 172, such that the at least one production float 114 is suspended in a submerged state within the ocean;
wherein the at least one production float 114 is connected to the heat collection device 102 with the at least one structural support cable 179, wherein a length 182 of the at least one structural support cable 179 is configured to be adjustable, for example via the use of winches and/or cable tighteners, such that a position of the heat collection device 102 is adjustable.

In another related embodiment, the carbon negative clean fuel production system 100 can further include:

a sand refinery machine 128, which is configured to refine sand 678 to produce chemical components, including silicon 674 and oxygen 676.

In another related embodiment, the carbon negative clean fuel production system 100 can further include:

a carbon removal system 106, which can be configured to use the electric energy generated by the heat-driven electric generator 118 to pump in atmospheric air 690, and to produce formic acid 694 or methane from carbon dioxide 692 in the atmospheric air 690, thereby reducing a concentration of carbon dioxide in the atmospheric air 690.

In a further related embodiment, the carbon removal system 106 can be configured to use the Sammels process, as described in PCT/International Patent Application number WO2014202855A1 and U.S. Pat. No. 4,673,473, such that the carbon removal system 106, is configured to produce formic acid from carbon dioxide and water by catalyzed electroreduction of the carbon dioxide in the gaseous phase, wherein the carbon removal system 106 uses electrochemical cells wherein a cathode consists of a conductive porous solid and an active layer containing dispersed metal nanoparticles, such that a catalyzed reaction produces the formic acid, which is separated by crystallization.

In a further related embodiment, the carbon removal system 106 can be configured to capture carbon dioxide from seawater, wherein the carbon removal system 106 can be configured to use the electric energy generated by the heat-driven electric generator to extract the carbon dioxide from seawater and react the carbon dioxide with hydrogen in a chemical process using a catalyst to produce a synthetic hydrocarbon, which comprises the carbon dioxide, and thereby binds the carbon dioxide, such that the hydrocarbon can be used as a fuel, such as disclosed in U.S. Pat. No. 7,420,004, which is hereby incorporated herein by reference in its entirety. As disclosed in U.S. Pat. No. 7,420,004, the chemical process can be a reverse water gas shift combined with Fischer Tropsch synthesis.

In a yet further related embodiment, the carbon dioxide can be extracted from the seawater by partial vacuum degassing, or other well-known physical or chemical extraction processes, or by a combination of any such extraction methods.

In another yet further related embodiment, the catalyst can include at least one of (or is selected from the group consisting of):

a) at least one or more metals selected from the group consisting of iron, cobalt, and nickel, and combinations thereof;
b) at least one or more metal oxides selected from the group consisting of iron oxide, cobalt oxide, nickel oxide, ruthenium oxide, and combinations thereof;
c) at least one or more support type materials selected from the group consisting of alumina, zeolites, and combinations thereof;
d) at least one or more other catalyst support selected from the group consisting of metals, metal oxides, metal alloys, mixed metal oxides, and combinations thereof; and
e) a combination of these.

Thus, in a related embodiment, the carbon negative clean fuel production system 100 can further include:

a mineral separator 115, which includes an enclosure 260 that comprises riffles 228 along an inner bottom of the enclosure;
wherein an input opening 262 of the enclosure 260 receives the hydrothermal emissions 141 from the hydrothermal vent 145, such that the hydrothermal emissions 141 pass through 266 the enclosure 260, such that solid minerals 280 are deposited in the riffles 228 and remaining emissions 268 are ejected from an output opening 264 of the enclosure 260.
a sand refinery machine 128, which is configured to refine sand 678 to produce chemical components, including silicon 674 and oxygen 676;
a chemical production system 120, which uses the silicon 674, oxygen 676, and solid minerals 280, to produce hydrides 682, halides 684, and silane 686.

In a related embodiment, as shown in FIG. 6B, the heat-driven electric generator 618 can be positioned directly adjacent to a hydrothermal vent 145 on a floor 152 of an ocean 650, such that the heat-driven electric generator 618 receives the heat from the hydrothermal vent 145 and produces electric energy 300.

Thus, in an alternative embodiment, as shown in FIG. 6B, a carbon negative clean fuel production system 600 can include:
- a heat-driven electric generator 118, which can be configured to receive heat from a hydrothermal vent 145 on a floor 152 of an ocean 650 and produce electric energy, wherein the heat-driven electric generator 618 can be positioned directly adjacent to a hydrothermal vent 145 on a floor 152 of an ocean 650, such that the heat-driven electric generator 118 receives the heat from the hydrothermal vent 145 and produces electric energy; and
- an electric distribution grid 300, which is configured to distribute the electric energy produced by the heat-driven electric generator 118.

In an embodiment, as illustrated in FIG. 8, a method for carbon negative clean fuel production system 800, can include:
- a) capturing heat 802 from hydrothermal emissions 141 from a hydrothermal vent 145 on a floor 152 of an ocean 650, using a heat collection device 102;
- b) producing electric energy 804, wherein a heat-driven electric generator 118 receives the heat from the hydrothermal vent 145 and produces the electric energy, wherein the heat is distributed via a heat distribution system 103;
- c) separating minerals 806, wherein solid minerals 280 are separated using a mineral separator 115, which comprises an enclosure 260 and riffles 228, which are positioned along an inner bottom 250 of the enclosure 260;
  - wherein an input opening 262 of the enclosure 260 receives the hydrothermal emissions 141 from the hydrothermal vent 145, such that the hydrothermal emissions 141 pass through the enclosure 260, such that the solid minerals 280 are deposited in the riffles 228 and remaining emissions 268 are ejected from an output opening 264 of the enclosure 260;
- d) filtering seawater 808, by using a seawater filtration unit 116, which is configured to filter seawater 652 from the ocean 650 by reverse osmosis, to produce filtered freshwater 654 and solutes 656 which include brine 656 and solute minerals 656;
- e) splitting the filtered freshwater 810, by using a water splitting device 107, which is configured to use the electric energy generated by the heat-driven electric generator 118 to split the filtered freshwater 654 into hydrogen 662 and oxygen 664 by a process of electrolysis;
- f) refining sand 812, by using a sand refinery machine 128, which refines sand 678 to produce chemical components, including silicon 674 and oxygen 676, wherein the sand refinery machine 128 uses the electric energy generated by the heat-driven electric generator 118;
- g) removing carbon dioxide from atmospheric air 814, by using a carbon dioxide removal system 106, which is configured to use the electric energy generated by the heat-driven electric generator 118 to pump in the atmospheric air 690, and to produce formic acid 694 from carbon dioxide 692 in the atmospheric air 690, thereby reducing a concentration of carbon dioxide in the atmospheric air 690; and
- h) producing hydrides, halides, and silane 816, by using a chemical production system 120, which uses the silicon 674, oxygen 676, and solid minerals 280, to produce the hydrides 682, the halides 684, and the silane 686, wherein the chemical production system 120 uses the electric energy 300 generated by the heat-driven electric generator 118.

In related embodiments, hydrides 682 produced by the chemical production system 120 can include ionic hydrides; covalent hydrides such as silane gas, synthetic gas, methane and ammonia; and metal hydrides, which for example can be used in batteries. Thus, such hydrides 682 produced by the chemical production system 120 can include carbon hydrides, jet fuel, diesel and gasolines, as well as metal hydrides for fuel cells.

It shall be understood that an executing instance of an embodiment of the carbon negative clean fuel production system 100, as shown in FIG. 1, can include a plurality of system control units 121.

FIGS. 1, 7 and 8 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1 and 7 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

FIG. 1 shows a depiction of an embodiment of the carbon negative clean fuel production system 100, including the system control unit 121, which can for example be configured as an embedded computer device 121, for example as a control board with a microcontroller or processor, or as a server 121. In this relation, a server shall be understood to represent a general computing capability that can be physically manifested as one, two, or a plurality of individual physical computing devices, located at one or several physical locations. A server can for example be manifested as a shared computational use of one single desktop computer, a dedicated server, a cluster of rack-mounted physical servers, a datacenter, or network of datacenters, each such datacenter containing a plurality of physical servers, or a computing cloud, such as Amazon EC2 or Microsoft Azure.

It shall be understood that the above-mentioned components of the system control unit 121 are to be interpreted in the most general manner.

For example, the processor 702, can include a single physical microprocessor or microcontroller, a cluster of processors, a datacenter or a cluster of datacenters, a computing cloud service, and the like.

In a further example, the non-transitory memory 704 can include various forms of non-transitory storage media, including random access memory and other forms of dynamic storage, and hard disks, hard disk clusters, cloud storage services, and other forms of long-term storage. Similarly, the input/output 706 can include a plurality of well-known input/output devices, such as screens, keyboards, pointing devices, motion trackers, communication ports, and so forth.

Furthermore, it shall be understood that the system control unit 121 can include a number of other components that are well known in the art of general computer devices, and therefore shall not be further described herein. This can include system access to common functions and hardware, such as for example via operating system layers such as Windows, Linux, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the system control unit 121 communicates with system objects over a network, which can include the general Internet, a Wide Area Network or a Local Area Network, or another form of communication network, transmitted on wired or wireless connections. Wireless networks can for example include Ethernet, Wi-Fi, Bluetooth, ZigBee, and NFC. The communication can be transferred via a secure, encrypted communication protocol.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the carbon negative clean fuel production system 100, and devices and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A carbon negative clean fuel production system, comprising:
    a) a heat collection device, which is configured to capture a heat from hydrothermal emissions from a hydrothermal vent on a floor of an ocean, wherein the heat collection device is configured to receive the hydrothermal emissions from the hydrothermal vent;
    b) a heat-driven electric generator, which is configured to receive the heat from the hydrothermal vent and produce electric energy;
    c) a seawater filtration unit, which is configured to filter seawater from the ocean, to produce filtered freshwater and solutes, which include brine and solute minerals;
    d) a water splitting device, which is configured to use the electric energy generated by the heat-driven electric generator to split the filtered freshwater into hydrogen and oxygen by a process of electrolysis;
    e) a mineral separator, which comprises an enclosure; wherein an input opening of the enclosure receives the hydrothermal emissions from the hydrothermal vent, such that the hydrothermal emissions pass through the enclosure, such that solid minerals are deposited in the mineral separator and remaining emissions are ejected from an output opening of the enclosure; and
    f) a chemical production system, which is configured to react the solid minerals with the hydrogen to produce hydrides.

2. The carbon negative clean fuel production system of claim 1, further comprising:

a direct pipe connection;
wherein the hydrothermal vent is an engineered hydrothermal vent;
such that the direct pipe connection is connected between the engineered hydrothermal vent and the heat collection device;
such that the heat collection device receives the hydrothermal emissions via the direct pipe connection.

3. The carbon negative clean fuel production system of claim 1, wherein the mineral separator further comprises riffles along an inner bottom of the enclosure, such that the solid minerals are deposited in the riffles.

4. The carbon negative clean fuel production system of claim 1, wherein the seawater filtration unit is configured to filter seawater from the ocean by reverse osmosis.

5. The carbon negative clean fuel production system of claim 1, further comprising:
at least one anchor tether;
at least one anchor structure;
at least one structural support cable; and
at least one production float, such that the production float is configured to be submerged, wherein the production float has a density less than seawater;
wherein the at least one production float is connected to the at least one anchor structure via the at least one anchor tether, such that the at least one production float is suspended in a submerged state within the ocean;
wherein the at least one production float is connected to the heat collection device with the at least one structural support cable, wherein a length of the at least one structural support cable is configured to be adjustable, such that a position of the heat collection device is adjustable.

6. The carbon negative clean fuel production system of claim 1, further comprising:
a sand refinery machine, which is configured to refine sand to produce chemical components, including silicon and oxygen.

7. The carbon negative clean fuel production system of claim 6, wherein the sand refinery machine is configured as an electric arc furnace, which is configured to perform a carbothermal reduction with the sand and a coke compound, to produce the silicon and the oxygen.

8. The carbon negative clean fuel production system of claim 1, further comprising:
a carbon dioxide removal system, which is configured to use the electric energy generated by the heat-driven electric generator to pump in atmospheric air, and to produce formic acid or methane from carbon dioxide in the atmospheric air, thereby reducing a concentration of carbon dioxide in the atmospheric air.

9. The carbon negative clean fuel production system of claim 8, wherein the carbon dioxide removal system is configured to use a Sammels process, such that the carbon dioxide removal system is configured to produce formic acid from the carbon dioxide by catalyzed electroreduction.

10. The carbon negative clean fuel production system of claim 8, wherein the carbon dioxide removal system is configured to use a Sabatier process, such that the carbon dioxide removal system is configured to produce methane from the carbon dioxide by reacting hydrogen with the carbon dioxide.

11. The carbon negative clean fuel production system of claim 1, further comprising:
a carbon dioxide removal system, which is configured to use the electric energy generated by the heat-driven electric generator to extract carbon dioxide from seawater and react the carbon dioxide with the hydrogen in a chemical process using a catalyst to produce a synthetic hydrocarbon.

12. The carbon negative clean fuel production system of claim 11, wherein the chemical process is a reverse water gas shift combined with Fischer Tropsch synthesis.

13. The carbon negative clean fuel production system of claim 11, wherein the catalyst comprises at least one of:
a) at least one metal selected from the group consisting of iron, cobalt, and nickel, and combinations thereof;
b) at least one metal oxide selected from the group consisting of iron oxide, cobalt oxide, nickel oxide, ruthenium oxide, and combinations thereof;
c) at least one support type material selected from the group consisting of alumina, zeolites, and combinations thereof;
d) at least one other catalyst support selected from the group consisting of metals, metal oxides, metal alloys, mixed metal oxides, and combinations thereof; and
e) a combination of these.

14. The carbon negative clean fuel production system of claim 1, wherein the chemical production system is configured to react to react metals of the solid minerals with the hydrogen under a high pressure and a high temperature to produce the hydrides, wherein the high pressure is at least 5 bars and the high temperature is at least 200 degrees Fahrenheit.

15. The carbon negative clean fuel production system of claim 1, further comprising:
a sand refinery machine, which is configured to refine sand to produce silicon; and
a chemical production system, which is configured to react the silicon with the hydrogen under a high pressure and a high temperature to produce silane;
wherein the high pressure is at least 5 bars and the high temperature is at least 200 degrees Fahrenheit.

16. A carbon negative clean fuel production system, comprising:
a heat-driven electric generator, which is configured to receive hydrothermal emissions from a hydrothermal vent on a floor of an ocean, such that the heat-driven electric generator receives a heat from the hydrothermal emissions and produces electric energy;
a seawater filtration unit, which is configured to filter seawater from the ocean, to produce filtered freshwater and solutes, which include brine and solute minerals;
a water splitting device, which is configured to use the electric energy generated by the heat-driven electric generator to split the filtered freshwater into hydrogen and oxygen by a process of electrolysis;
a mineral separator, which comprises an enclosure;
wherein an input opening of the enclosure receives the hydrothermal emissions from the hydrothermal vent, such that the hydrothermal emissions pass through the enclosure, such that solid minerals are deposited in the mineral separator and remaining emissions are ejected from an output opening of the enclosure; and
a chemical production system, which is configured to react the solid minerals with the hydrogen to produce hydrides.

17. The carbon negative clean fuel production system of claim 16, further comprising:
a direct pipe connection;
wherein the hydrothermal vent is an engineered hydrothermal vent;

such that the direct pipe connection is connected between the engineered hydrothermal vent and the heat-driven electric generator;

such that the heat-driven electric generator receives the hydrothermal emissions via the direct pipe connection.

18. The carbon negative clean fuel production system of claim 16, further comprising:

a carbon dioxide removal system, which is configured to use the electric energy generated by the heat-driven electric generator to extract carbon dioxide from seawater and react the carbon dioxide with hydrogen in a chemical process using a catalyst to produce a synthetic hydrocarbon.

19. A method of carbon negative clean fuel production, comprising:

a) capturing heat from hydrothermal emissions from a hydrothermal vent on a floor of an ocean, using a heat collection device;

b) producing electric energy, wherein a heat-driven electric generator receives the heat from the hydrothermal vent and produces the electric energy;

c) filtering seawater, by using a seawater filtration unit, which is configured to filter seawater from the ocean, to produce filtered freshwater and solutes which include brine and solute minerals;

d) splitting the filtered freshwater, by using a water splitting device, which is configured to use the electric energy generated by the heat-driven electric generator to split the filtered freshwater into hydrogen and oxygen by a process of electrolysis;

e) separating minerals, wherein minerals are separated using a mineral separator, which comprises an enclosure;

wherein an input opening of the enclosure receives the hydrothermal emissions from the hydrothermal vent, such that the hydrothermal emissions pass through the enclosure, such that solid minerals are deposited in the mineral separator and remaining emissions are ejected from an output opening of the enclosure; and f) producing hydrides, by using a chemical production system, which reacts the solid minerals with the hydrogen to produce hydrides, wherein the chemical production system uses the electric energy.

20. The method of carbon negative clean fuel production of claim 19, further comprising:

refining sand, by using a sand refinery machine, which is configured to extract the sand from the hydrothermal emissions, and refine the sand to produce chemical components, including silicon and oxygen.

21. The method of carbon negative clean fuel production of claim 19, further comprising:

removing carbon dioxide from atmospheric air, by using a carbon dioxide removal system, which is configured to use the electric energy generated by the heat-driven electric generator to pump in the atmospheric air, and to produce formic acid from carbon dioxide in the atmospheric air, thereby reducing a concentration of carbon dioxide in the atmospheric air.

22. The method of carbon negative clean fuel production of claim 19, further comprising:

extracting carbon dioxide from seawater and reacting the carbon dioxide with the hydrogen in a chemical process using a catalyst to produce a synthetic hydrocarbon.

23. A carbon negative clean fuel production system, comprising:

a) a heat collection device, which is configured to capture a heat from hydrothermal emissions from a hydrothermal vent on a floor of an ocean, wherein the heat collection device is configured to receive the hydrothermal emissions from the hydrothermal vent;

b) a heat-driven electric generator, which is configured to receive the heat from the hydrothermal vent and produce electric energy;

c) at least one anchor tether;

d) at least one anchor structure;

e) at least one structural support cable; and f) at least one production float, such that the production float is configured to be submerged, wherein the production float has a density less than seawater;

wherein the at least one production float is connected to the at least one anchor structure via the at least one anchor tether, such that the at least one production float is suspended in a submerged state within the ocean;

wherein the at least one production float is connected to the heat collection device with the at least one structural support cable, wherein a length of the at least one structural support cable is configured to be adjustable, such that a position of the heat collection device is adjustable.

24. The carbon negative clean fuel production system of claim 23, further comprising:

a seawater filtration unit, which is configured to filter seawater from the ocean, to produce filtered freshwater and solutes, which include brine and solute minerals.

25. The carbon negative clean fuel production system of claim 24, further comprising:

a water splitting device, which is configured to use the electric energy generated by the heat-driven electric generator to split the filtered freshwater into hydrogen and oxygen by a process of electrolysis.

26. The carbon negative clean fuel production system of claim 25, further comprising:

a carbon dioxide removal system, which is configured to use the electric energy generated by the heat-driven electric generator to extract carbon dioxide from seawater and react the carbon dioxide with the hydrogen in a chemical process using a catalyst to produce a synthetic hydrocarbon.

27. The carbon negative clean fuel production system of claim 26, wherein the chemical process is a reverse water gas shift combined with Fischer Tropsch synthesis.

28. The carbon negative clean fuel production system of claim 26, wherein the catalyst comprises at least one of:

a) at least one metal selected from the group consisting of iron, cobalt, and nickel, and combinations thereof;

b) at least one metal oxide selected from the group consisting of iron oxide, cobalt oxide, nickel oxide, ruthenium oxide, and combinations thereof;

c) at least one support type material selected from the group consisting of alumina, zeolites, and combinations thereof;

d) at least one other catalyst support selected from the group consisting of metals, metal oxides, metal alloys, mixed metal oxides, and combinations thereof; and e) a combination of these.

29. The carbon negative clean fuel production system of claim 25, further comprising:

a mineral separator, which comprises an enclosure;

wherein an input opening of the enclosure receives the hydrothermal emissions from the hydrothermal vent, such that the hydrothermal emissions pass through the enclosure, such that solid minerals are deposited in the mineral separator and remaining emissions are ejected from an output opening of the enclosure; and a chemical production system, which is configured to react the solid minerals with the hydrogen to produce hydrides.

\* \* \* \* \*